United States Patent [19]
Fletcher et al.

[11] 4,061,570
[45] Dec. 6, 1977

[54] IODINE GENERATOR FOR RECLAIMED WATER PURIFICATION

[76] Inventors: James C. Fletcher, Administrator of the National Aeronautics and Space Aministraton, with respect to an invention of; Richard A. Wynveen, Pepper Pike; James D. Powell, Euclid; Franz H. Schubert, Mentor, all of Ohio

[21] Appl. No.: 571,459

[22] Filed: Apr. 25, 1975

[51] Int. Cl.² .................... B01J 1/06; B01J 4/02; G01N 21/02; G01N 33/18
[52] U.S. Cl. ............... 210/96 M; 210/192; 204/180 P; 204/301; 23/253 A
[58] Field of Search ............. 23/253 A; 210/62, 64, 210/96, 192; 204/180 P, 301

[56] References Cited
U.S. PATENT DOCUMENTS

| | | | |
|---|---|---|---|
| 3,288,708 | 11/1966 | Cordle et al. | 210/62 |
| 3,351,542 | 11/1967 | Oldershaw et al. | 210/62 |
| 3,464,555 | 9/1969 | Schneider | 210/96 |
| 3,528,545 | 9/1970 | Frazel et al. | 210/96 |
| 3,554,905 | 1/1971 | Place et al. | 210/62 |
| 3,574,084 | 4/1971 | Bruce | 210/62 |
| 3,669,857 | 6/1972 | Kirkham et al. | 204/180 P |
| 3,755,134 | 8/1973 | Francis et al. | 204/180 P |

*Primary Examiner*—Morris O. Wolk
*Assistant Examiner*—Bradley Garris
*Attorney, Agent, or Firm*—Carl O. McClenny; John R. Manning; Marvin F. Matthews

[57] ABSTRACT

The system disclosed is for controlling the iodine level in a water supply in a spacecraft. The system iodinates drinking water as necessary. It includes an iodine accumulator which stores crystalline iodine, an electro-chemical valve to control the input of iodine to the drinking water and an iodine dispenser. A pump dispenses fluid through the iodine dispenser and an iodine sensor to a potable water tank storage. The iodine sensor electronically detects the iodine level in the water, and through electronic means, produces a correction current control. The correction current control operates the electro-chemical iodine valve to release iodine from the iodine accumulator into the iodine dispenser.

7 Claims, 3 Drawing Figures

IODINE GENERATOR FOR RECLAIMED WATER PURIFICATION

ORIGIN OF THE INVENTION

The invention described herein was made in the performance of work under a NASA Contract and is subject to the provisions of Section 305 of the National Aeronautics and Space Act of 1958, Public Law 85-568 (72 Statute 435; 42 U.S.C. 2456).

FIELD OF THE INVENTION

This invention relates to systems for controlling the iodine level in the water supply for a spacecraft. More particularly, this system relates to an electro-chemical iodine valve which can be operated by an electrical current in response to detection of iodine levels in the water supply to inject additional iodine into the water system in precise and controlled amounts to maintain a preset residual concentration of iodine in the water supply.

BACKGROUND OF THE INVENTION

In a spacecraft as well as other situations where micro-organism control of drinking water is desired, iodine is a suitable agent. Iodine has several notable characteristic advantages as a micro-organism control and is effective against a broad spectrum of organisms. Ordinarily, in a spacecraft operation, it is desirable to maintain low weight requirement and low electrical power consumption. In this invention the valve operates at 10 mWatts and 5 ma. The spacecraft uses recycled water. The iodine system is superior to pasteurization on the basis of weight, volume, cost and power consumption.

SUMMARY OF THE INVENTION

The system for iodination of water includes a potable water storage tank. Water is circulated by a pump to the storage tank through a dispenser chamber which has an iodine valve. From the dispenser chamber, the water passes through an iodine sensor to the potable water storage tank. The iodine sensor detects the level of iodine concentration in the water and produces in response thereto electrical signals. The electrical signals are sampled and passed to an error amplifier which determines if the iodine level is below a predetermined or preset value. If an error signal is produced, a corresponding current is passed through the electro-chemical iodine valve to pass iodine into the water by ion exchange.

The electro-chemical iodine valve includes an anion exchange membrane. An anode and cathode are respectively disposed on opposite sides of the membrane. On one side of the membrane a slurry of water and $I_2$ crystals are stored. On the other side of the membrane, the water supply circulates past the membrane in the dispenser chamber. An electrical current between the anode and cathode causes iodine to transfer from one side of the membrane to the other side of the membrane.

DESCRIPTION OF THE PREFERRED EMBODIMENT

Figure 1:
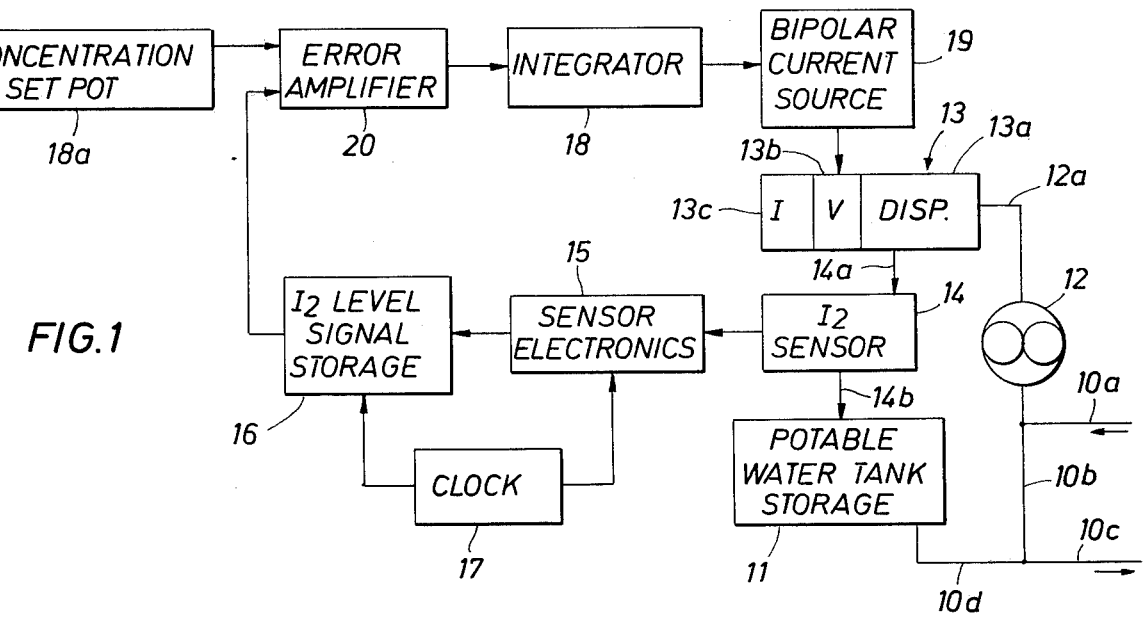
FIG. 1 is a schematic illustration of the system embodying the present invention.

One type of system is illustrated in FIG. 1. Conduits 10(a-c) are part of a system in which potable water is circulated. Additional water as necessary for the system is supplied to an output conduit 10c from a water storage tank 11 via a conduit 10d. An input conduit 10a is coupled by a pump 12 to an iodinating device 13. In the iodinating device 13 is a dispensing compartment 13a, an electro-chemical valve 13b, and an $I_2$ accumulator 13c. The $I_2$ accumulator 13c contains a slurry of iodine crystals and water. The valve 13b is electrically controlled to pass iodine into the dispensing compartment 13a. Water from the system is passed through the dispensing compartment 13a and is in contact with the electro-chemical valve 13b.

The output from the dispensing compartment 13a is coupled to an iodine level sensing means 14 which detects the iodine level in the water for the system. The iodine sensing means 14 is coupled to the water storage tank 11. Insofar as water flow is concerned, it passes from the pump 12 through the dispensing compartment 13a and iodine sensing means 14 to the storage tank 11. The storage tank 11 is coupled to the output conduit 10c.

The iodine sensing means 14 continuously detects the level of iodine concentration in the water and produces analog electrical signals representative or proportional to the iodine concentration in the water. The electrical signals representative of iodine concentration are supplied to sensor electronic means 15 which convert the analog electrical signals into digital signals. A signal storage means 16 is coupled to the sensor electronic means 15 to receive stored digital signals from the electronic means 15 and to output analog signals. A clock, 17, which can be a free running multivibrator and include a divider circuit, functions to initiate the sensor electronic means 15 to obtain an iodine level reading from the sensor means 14. After a signal is stored, the clock causes the signal to be output from the storage means 16. Thus the concentration is measured at discrete times which can be one minute or longer.

The output signals from the storage means 16 are supplied to an error amplifier means 20. The error amplifier means 20 is also input with a calibrated electrical signal from a potentiometer 18a. The potentiometer signal is representative of a desired iodine level or concentration in the water. If the iodine level decreases in the water, an output signal is produced by the error amplifier 20 to an integrator means 18 which operates a bipolar current source 19. The bipolar current source is responsive to the output of the integrator 18 to provide a control current for the valve 13b.

In the foregoing system, the sampling is periodic. If continuous sampling is desired, the signals from the $I_2$ sensor 14 are supplied via an amplifier (not shown) directly to the error amplifier 20.

Figure 2:
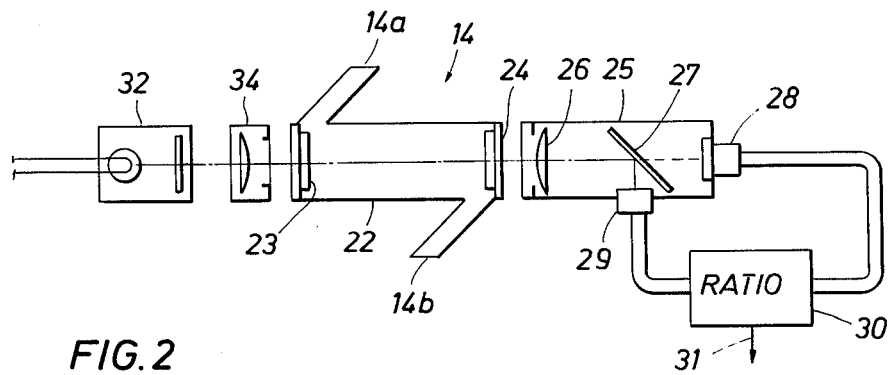
FIG. 2 is a schematic illustration of an $I_2$ sensor for the system.

Referring now to FIG. 2, the iodine sensor means 14 includes a tubular chamber 22 with flow inlets 14a and 14b at opposite ends. The flow inlet 14a is angled with respect to the axis of chamber 22 so that fluid flow into the chamber 22 via the inlet 14a has an impinging and washing action on a glass lens 23 which also serves as an end cap. The outlet 14b similarly is angled with respect to the axis of chamber 22 so that a washing action occurs (as fluid exits from the chamber) on an end cap glass lens 24. A detector 25 is aligned with the axis of chamber 22 and includes a glass lens 26, a 45° beam splitter mirror 27 and light sensors 28 and 29 aligned at 90° relative to one another and relative to the axis of the detector 25 and to the mirror 27. The light sensors 28 and 29 are respectively coupled to a ratio circuit 30 which provides an output if the ratio between the input signals varies. A light source 32 and lens 34 provide light for transmission through the cell 22 to the light sensors 28 and 29. The sensors 28 and 29 are respectively provided with a 465 mm interference filter and a 630 nm interference filter. Thus, a given ratio of signals will be indicative of a given iodine level or concentration in the water supply. As the iodine is used and its level decreases, the ratio changes to produce an output signal on line 31.

Figure 3:
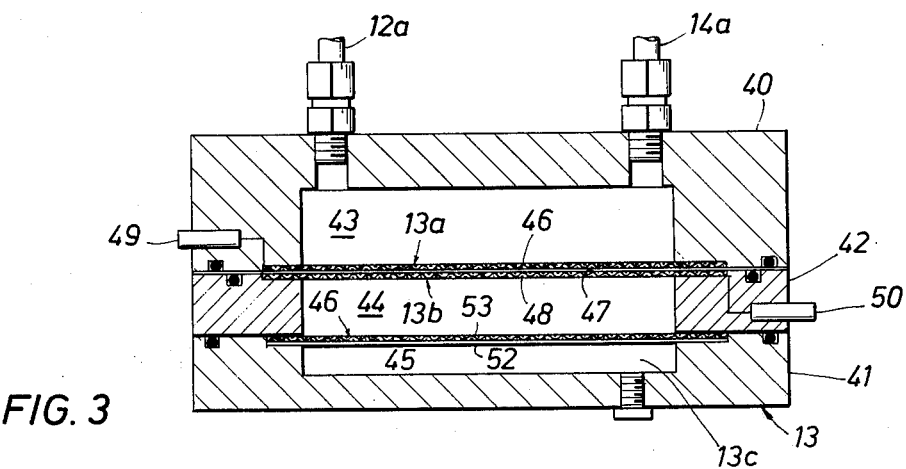
FIG. 3 is a view in cross-section through an iodinating device embodying the principles of the present invention.

The iodinating device 13 of the present invention is illustrated in detail in FIG. 3. The iodinating device has a generally rectangular box-like configuration with end members 40 and 41 and a center member 42. The members define an interior cavity which is divided into three chamber sections 43, 44 and 45. Chamber section 43 is defined by the end interior walls of the member 40 and a valve means 13a. The middle chamber section 44 is defined between the valve means 13b and a retainer screen 46. The chamber section 45 is defined between the retainer screen 46 and the interior walls of the member 41.

The valve 13b is comprised of a center, flat member 47 and outer, flat metal screens 46 and 48 which form electrodes. The membrane provides for ion exchange. The anode electrode 46 is made of a noble metal and coupled to an outlet terminal 49 and the cathode electrode is made of a noble metal and is coupled to an outlet terminal 50. When an electrical potential is applied across the anode and cathode 46 and 48, the membrane 47 permits an ion exchange. The chamber sections 44 and 45 are fluidly interconnected and in chamber section 45 is a slurry of water and $I_2$ crystals. A perforated sheet 52 which can be plexiglass, together with a stainless steel screen 53 retains the crystals in the section 45. The chamber section 44 contains dissolved $I_2$ in solution. $I_2$ crystals are advantageous for this application because they are solid at room temperature.

The anion exchange membrane 47 is preconditioned by soaking in a stirred solution of 0.6 potassium iodine solution for one-half hour. The membrane is then rinsed and again soaked this time in a 0.1 normal potassium iodide solution for one-half hour. The second step of rinsing and soaking is then repeated. The membrane immobilizes the iodine and prevents the water being iodinated from contacting solid $I_2$ crystals.

When a current is passed between the anode and cathode, the reactions occurring at the electrodes are:

| Anode | $2I^-$ | | $= I_2$ | $+ 2e^-$ |
|---|---|---|---|---|
| | $I_3^-$ | | $= I_2$ | $+ I^-$ |
| Cathode | $I_2$ | $+ 2e^-$ | $= 2I^-$ | |
| | $I_2$ | $+ I^-$ | $= I_3$ | |

The membrane is conductive to anions ($I^-$, $I_3^-$ and $OH^-$) and the cation portion of the electrolyte is immobilized within the membrane. Hydrogen ions, water, $I_2$, HOI, etc., do not pass through the membrane as a result of the anion exchange mechanism.

It will be appreciated that the iodinating means 13 can continuously iodinate the water passing through the dispenser where the accumulator stores crystalline iodine and the electro-chemical valve controls the flow of iodine to the water supply.

In the operation system, a pump circulates liquid to be iodinated through the iodination means 13, the sensor 14 and the storage tank 11. The $I_2$ level sensed by the sensor 14 produces electrical signals which are compared with an established $I_2$ level set point signal (set pot 18). Any difference in voltage between these signals (the error) is sent to an integrator 18. The integrator 18 has an output which is constant only when its input voltage is zero. The integrator output signal is used to control the bipolar current source circuit 19 which, in turn, produces a constant current directly proportional to the signal received at its input. The valve 13b generates iodine ions and dispenses ions into the liquid loop as a function of the electrical current flowing through it.

In this system, the sensor signal and set point signal must be equal to cause the valve to release as much $I_2$ as is being consumed. If the $I_2$ level in the circulatory loop should decrease, the output from the error amplifier will increase from zero which will cause the output of the integrator to start increasing. This causes a higher current generation and therefore a higher $I_2$ dispensing rate.

To use the sensor to measure discontinuously, the storage system 16 is inserted between the sensor 15 and error amplifier 20. The clock 17 times the control sampling and inputs. The amplifier 20 and integrator 18 operate to increase current values to a point when $I_2$ generation and consumption are equal. The $I_2$ sensor measures $I_2$ concentration at discrete time intervals of one minute or longer. The sensor signal storage circuit 16 accepts an $I_2$ level signal and stores it until a new sensor signal is obtained. When a signal from the $I_2$ system is to be stored, a clock system will cause the $I_2$ sensor signal to be converted to an eight-bit digital number that is stored. Output from the storage circuit 16 is converted from digital to analog signals which are used in the $I_2$ control system. The stored signal is assumed to be the latest $I_2$ control signal representative of the latest $I_2$ concentration and will be maintained until a new clock signal is received, at which time the system will store the updated $I_2$ sensor signal. By storing the digital form of the $I_2$ sensor signal, the length of time which the signal is stored can be extended indefinitely. The system clock 17 is a freerunning oscillator feeding an eight-bit binary divider. Outputs from the binary divider intitiate a signal to the $I_2$ sensor 15 to initiate a reading. The other output provides a signal to initiate storage in the storage circuit 16. These two signals occur at different times so that the sensor 14 is automatically instructed to measure and, after the measurement, the signals are allowed to stabilize and are stored.

Suitable non-metallic materials for use in the iodinating means include polypropylene, plexiglass, teflon, epoxy resins, polysulfones, polyamides and nylons. Stainless steel is a suitable metallic material and platinum is a suitable noble metal to use for the anode and cathode.

Based upon iodine spectroscopy, the absorption characteristics for $I_2$ are such that at a wavelength of 466 nm a crossover point exists where for a given concentration of iodine the absorption is constant. This is an "isobestic point" and at this wavelength iodine can be measured unaffected by varying amounts of potassium iodide. The sensor 14 is intended to measure iodine at a wavelength of 466 nm. A dual detector, dual wavelength system is used and the light measurements are taken at two different wavelengths. In the sampling section, which is made of anodized aluminum and fitted with heat-absorbing glass windows, water enters and leaves at an angle thereby generating a washing action on the windows. In the detector section 25, there is a beam splitter and two detectors 28 and 29. Collimated light from the light cell are focused onto separate detectors by virtue of a beam splitter. The beam splitter transmits light through a 465 nm interference filter to a sample detector and reflects light through a 630 nm filter to the reference detector. The beam splitter 27 permits each detector to "see" the same area of the sample cell window, thus any localized variation in the window clarity will not influence the output of one detector more than that of the other.

While particular embodiments of the present invention have been shown and described, it is apparent that changes and modifications may be made without departing from this invention in its broader aspects; and therefore, the aim in the appended claims is to cover all such changes and modifications as fall within the true spirit and scope of this invention.

What is claimed is:

1. A system for iodinating water comprising
   a. an iodine dispensing means having a first and a second chamber separated by an electro-chemical valve means, said first chamber being adapted to receive a slurry of iodine crystals, said second chamber having an inlet and an outlet for the flow of water to be iodinated, said electro—chemical valve means having an anion exchange membrane sandwiched between two metal screens which form electrodes, each of said metal screen electrodes being electrically coupled to an outlet terminal, said electro-chemical valve means being responsive to an electrical current for passing iodine across said anion exchange membrane,
   b. an iodine sensor means for detecting the concentration of iodine in the iodinated water, said iodine sensor means having an inlet and an outlet for the flow of iodinated water, said inlet for the iodine sensor means being fluidly coupled to said outlet of the second chamber of the iodine dispensing means, said iodine sensor means further having means for producing an electrical signal representative of the iodine concentration in the iodinated water flowing through the iodine sensor means,
   c. reference means for providing a present electrical signal representative of a desired iodine concentration,
   d. comparator means electrically coupled to said iodine sensor means and said reference means for comparing the electrical signal from said iodine sensor means with the electrical signal from said reference means and for producing an error signal in the event of a difference in signal values, and
   e. means for supplying said error signal to said outlet terminals of said electrodes.

2. The system of claim 1 wherein said anion exchange membrane is impregnated with potassium iodide.

3. The system of claim 1 wherein a perforated member is disposed in said first chamber adapted to separate crystalline iodine in a slurry of iodine crystals from said anion exchange membrane.

4. The system of claim 1 wherein said electrodes are comprised of a noble metal.

5. The system of claim 4 wherein said noble metal is platinum.

6. The system of claim 1 wherein said electrodes are comprised of platinum screens, said anion exchange membrane is impregnated with potassium iodide, and said first chamber has disposed therein a slurry of iodine crystals.

7. The system of claim 6 wherein a perforated member is disposed in said first chamber so that the iodine crystals are separated from said anion exchange membrane.

* * * * *